(12) United States Patent
Kennedy et al.

(10) Patent No.: US 6,998,235 B2
(45) Date of Patent: Feb. 14, 2006

(54) METHOD OF DETERMINING SUSCEPTIBILITY TO BIPOLAR DISORDERS

(75) Inventors: James L. Kennedy, Toronto (CA); Pierandrea Muglia, Toronto (CA)

(73) Assignee: Centre for Addiction and Mental Health, Toronto (CA)

( * ) Notice: Subject to any disclaimer, the term of this patent is extended or adjusted under 35 U.S.C. 154(b) by 579 days.

(21) Appl. No.: 10/170,356

(22) Filed: Jun. 14, 2002

(65) Prior Publication Data

US 2003/0087269 A1 May 8, 2003

Related U.S. Application Data

(60) Provisional application No. 60/298,120, filed on Jun. 15, 2001.

(51) Int. Cl.
*C12Q 1/68* (2006.01)

(52) U.S. Cl. .......................................... 435/6; 435/91.2
(58) Field of Classification Search .................... 435/6; 536/23.1, 24.31, 24.33, 23.5
See application file for complete search history.

(56) References Cited

U.S. PATENT DOCUMENTS

| | | | |
|---|---|---|---|
| 6,132,724 A | 10/2000 | Blum et al. ................. | 424/725 |
| 6,203,998 B1 | 3/2001 | Civelli et al. .............. | 435/7.21 |

OTHER PUBLICATIONS

Bocchetta, A. et al., "Family-Based Association Study Between Biopolar disorder and DRD2, DRD4, DAT and SERT in Sardinia", American Journal of Medical Genetics, 1999, pp. 522-526, vol. 88.

Furlong, R. A. et al., "Analysis and Metaanalysis of Two Polymorphisms Within the Tyrosine Hydroxylase Gene in Bipolar and Unipolar Affective Disorders", American Journal of Medical Genetics, 1999, pp. 88-94, vol. 88.

Jovanovic, V. et al., "Comparative pharmacological and functional analysis of the human dopamine $D_{4\ 2}$ and $D_{4\ 10}$ receptor variants", Pharmacogentics, 1999. pp. 561-568, vol. 9.

Lichter, J. B. et al., "A hypervariable segment in the human dopamine receptor $D_4$ (DRD-4) gene", Human Molecular Genetics, 1993, pp. 767-773, vol. 2, No. 6.

Lim, L. C. C. et al., "No Evidence of Association Between Dopamine D4 Receptor Variants and Bipolar Affective Disorder", American Journal of Medical Genetics, 1994, pp. 259-263, vol. 54.

Muglia, P. et al., "Dopamine D4 receptor and tyrosine hydroxylase genes in bipolar disorder: evidence for a role of DRD4", Molecular Psychiatry, 2002, pp. 1-7.

Van Tol, H. H. M. et al., "Multiple dopamine D4 receptor variants in the human population", Nature, 1992, pp. 149-152, vol. 358.

Van Tol, H. H. M. et al., "Cloning of the gene for human dopamine $D_4$ receptor with high affinity for the antipsychotic clozapine". Nature, 1991, pp. 610-614, vol. 350, No. 6319.

Asghari, V. et al., "Modulation of Intracellular Cyclic AMP Levels by Different Human Dopamine D4 Receptor Variants", Journal of Neurochemistry, 1995, pp. 1157-1165, vol. 65, No. 3.

Ding, Y. C. et al., "Evidence of positive selection acting at the human dopamine receptor D4 gene locus". PNAS, 2002, pp. 309-314, vol. 99, No. 1.

Chang, F. M. et al., "The world-wide distribution of allele frequencies at the human dopamine D4 receptor locus", Hum Genet, 1996, pp. 91-101, vol. 98.

De Bruyn. A. et al., "Nonlinkage of Bipolar Illness to Tyrosine Hydroxylase, Tyrosinase. and $D_2$ and $D_4$ Dopamine Receptor Genes on Chromosome 11". American Journal of Psychiatry, 1994, pp. 102-106, vol. 151, No. 1.

Serretti, A. et al., "Genetic variants of dopamine receptor D4 and psychopathology", Schizophrenia, 1999, pp. 609-618, vol. 23, vol. 3.

Serretti. A. et al., "Dopamine receptor D4 gene is not associated with major psychoses", Am. J. Med. Genet., 1999, pp. 486-491, vol. 88, No. 5.

Serretti, A. et al., "DRD4 exon 3 variants associated with delusional symptomatology in major psychoses: a study on 2,011 affected subjects". Am. J. Med. Genet. 2001, pp. 283-290, vol. 8, No. 105.

*Primary Examiner*—James Martinell
(74) *Attorney, Agent, or Firm*—Micheline Gravelle Bereskin & Parr

(57) ABSTRACT

Methods and kits for determining susceptibility of a patient to bipolar disorders are described. The method comprises the steps of: (a) obtaining a sample from a patient; and (b) testing the sample for the presence of a polymorphism selected from (i) a 2 repeat allele in the variable number of tandem repeat (VNTR) region of the DRD4 gene and (ii) a 4 repeat allele in the VNTR region of the DRD4 gene, wherein the presence of the 2 repeat allele indicates that the patient is less susceptible to a bipolar disorder and the presence of the 4 repeat allele indicates that the patient is more susceptible to a bipolar disorder.

10 Claims, No Drawings

METHOD OF DETERMINING SUSCEPTIBILITY TO BIPOLAR DISORDERS

FIELD OF THE INVENTION

The present invention relates to methods and kits for determining susceptibility of a patient to bipolar disorders.

BACKGROUND OF THE INVENTION

Family, twin and adoption study demonstrated evidence for importance of genetic factors in bipolar disorder (Gershon et al 1990). The mode of inheritance does not follow the Mendelian rules and multiple genes (Risch and Botsein 1996) with likely complex gene-gene (Berrettini 1999) and gene-environment interaction are likely to be involved.

Different linkage studies have investigated the short arm of chromosome 11 in bipolar families since the first evidence for linkage in an Old Order Amish kindred (Egeland et al 1987). This finding however was not replicated in the reanalysis of the families after the disease occurred in some individuals that were unaffected in the primary analysis (Kelsoe et al 1989). Further linkage studies of 11p in several data sets of bipolar families have failed to show consistent results (Detera-Wadleigh et al 1987; Nothen et al 1990; Byerley et al 1992; Sidenberg et al 1994; Smyth et al 1996; Smith et al 1997; Malafosse et al 1997).

Interestingly, the short arm of chromosome 11 on p15.5 harbors two dopamine system genes, i.e. the dopamine D4 receptor (DRD4) and the tyrosine hydroxylase (TH) genes, which are both of interest for bipolar disorder. Preliminary evidence for the involvement of dopamine pathways in bipolar disorder aroused from animal studies, more recently evidence from pharmacological and behavioural studies in humans continue to support a dopaminergic role in the etiology of bipolar disorder (Willner 1995).

The gene for the dopamine D4 receptor is highly polymorphic, containing a functional variable number of tandem repeat (VNTR) in the third exon, the region of the gene that encodes for the intracellular loop of the receptor (Van Tol et al 1992; Asghari et al 1995). The polymorphism consists of 2 to 11 imperfect tandem repeat of 48 bp, coding for 16 amino acids. Thirty-five variations of the sequence within the 48 bp repeat, that generate 56 haplotypes, have been described (Lichter et al, 1993; Ding et al 2002). Most of these haplotypes are extremely rare with a frequency of less than 1%. Each of the repeat alleles has one variant that is much more common than the others, for example the most common variant of the 4 repeat allele has a frequency of 95% (Ding et al 2002). In vitro studies have found different pharmacological properties for the D4 receptors coded by the 2, 4 7 and 10 repeat alleles (Asghari et al 1995, Jovanovic et al 1999). Tyrosine hydroxylase is the rate-limiting enzyme in the synthesis of catecholamines that converts tyrosine to DOPA. Its gene contains a microsatellite in the Intron I constituted by a tetranucleotide repeat of $(TCAT)_n$ motif (HUMTH01) that can be repeated five to 10 times (Polymeropulos et al 1991), the 10 repeat alleles can be present in two different sequence variants (Puers a et al 1993). A recent in vitro study suggests that the microsatellite HUMTH01 may be implicated in the regulation of the gene expression (Meloni et al 1998).

There remains a need to identify genetic polymorphisms that may be useful in determining a person's susceptibility to bipolar disorders.

SUMMARY OF THE INVENTION

The present inventors have shown that there is an increased number of non-transmitted DRD4 2 repeat alleles and an increased number of transmissions for the 4 repeat alleles to bipolar patients when compared to what should be expected by chance. This effect was derived almost exclusively from the maternal meiosis. The excess of non-transmission of the 2 alleles to bipolar patients suggests that the 2 repeat allele may confer a protective role while the 4 repeat alleles may increase the risk in developing bipolar disorder when transmitted from the maternal side. Because of the occurrence in the human population of multiple sequences within the 48 bp repeat all the 2 repeat alleles that were informative from the maternal meioses were sequenced. No sequence variants for the 2 repeat allele were found.

The present invention therefore relates to a method of determining the susceptibility of a patient to a bipolar disorder comprising:

(a) obtaining a sample from a patient; and (b) testing the sample for the presence of a polymorphism selected from (i) a 2 repeat allele in the variable number of tandem repeat (VNTR) region of the DRD4 gene and (ii) a 4 repeat allele in the VNTR region of the DRD4 gene, wherein the presence of the 2 repeat allele indicates that the patient is less susceptible to a bipolar disorder and the presence of the 4 repeat allele indicates that the patient is more susceptible to a bipolar disorder.

Preferably the polymorphisms are transmitted from the maternal side. Therefore the present invention also relates to a method of determining the susceptibility of a patient to a bipolar disorder as defined above, further comprising:

(c) obtaining a sample from the patient's mother;

(d) testing the mother's sample for the presence of a polymorphism selected from (i) a 2 repeat allele in the variable number of tandem repeat (VNTR) region of the DRD4 gene and (ii) a 4 repeat allele in the VNTR region of the DRD4 gene, wherein the presence of a 2 repeat allele from the mother in the sample from the patient indicates that the patient is less susceptible to a bipolar disorder and the presence of a 4 repeat allele from the mother in the sample from the patient indicates that the patient is more susceptible to a bipolar disorder.

In another embodiment of the invention, there are provided methods of detecting the presence of a polymorphism in the DRD4 gene associated with a bipolar disorder.

The present invention also provides a kit for determining susceptibility of a patient to a bipolar disorder, or for detecting the presence of a polymorphism associated with a bipolar disorder, comprising reagents necessary for determining the presence of a polymorphism selected from a 2 repeat allele in the VNTR region of the DRD4 gene and a 4 repeat allele in the VNTR region of the DRD4 gene and directions for its use.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

The inconsistencies shown across the linkage studies that investigated the short arm of chromosome 11 in bipolar disorder do not exclude the possible small contribution of genes to disease (for e.g. DRD4 and TH) since linkage analysis has low power to detect genes with partial contribution to disease (Greenberg 1993). Association studies that investigated the role of DRD4 in bipolar disorder did not show evidence for association (De bruyn et al 1994; Serretti et al 1999; Lim et al 1994; Li et al 1999; Bocchefta et al 1999). In a similar fashion, the association studies of HUMTH01 in bipolar disorder produced positive and negative association and a meta-analysis of these studies showed no major effect attributable to the HUMTH01 in bipolar disorder (Reviewed in Furlong et al 1999). However, because the majority of studies that investigated DRD4 were case-controls and the only study conducted on families was in a small sample size (Bochetta et al 1999), the involvement of DRD4 in bipolar disorder cannot be ruled out. The case-control approach, in fact, is associated with the risk of producing spurious results because of the difference in allele frequencies across different populations (Kidd 1993). Limits of case-control studies are particularly evident when the candidate genes being studied have a demonstrated population-specific frequency for their alleles, as in the case of the DRD4 exon III VNTR (Chang et al 1999). Family-based association studies prevent the occurrence of false positive results derived from population stratification (Ott 1999), have good power to detect genes with partial effects as compared to linkage strategies, and allows the separate analysis of maternally and paternally transmitted alleles. Although the statistical power of family studies is lower when compared to case-control strategies (Rish 2000), maternal and paternal meiosis may help in understanding the presence of type I errors from true association (Petronis 2000). In the present study a family-based association study of the DRD4 48 bp repeats VNTR and the TH intron I tetranucleotide repeats VNTR allele was performed in a sample made up of subjects suffering from DSM IV bipolar disorder and their respective biological parents.

The results of the present study showed an increased number of non-transmitted DRD4 2 repeat alleles and an increased number of transmissions for the 4 repeat alleles when compared to what should be expected by chance. This effect was derived almost exclusively from the maternal meiosis. The excess of non-transmission of the 2 alleles to bipolar patients is suggesting that the 2 repeat allele may confer a protective role while the 4 repeats alleles may increase the risk in developing bipolar disorder, when transmitted from the maternal side. Furthermore, the effect of the maternal meioses in the biased transmission of the 4-repeat allele was stronger when the families with a maternal history of bipolar disorder were considered (for the 4 repeat allele 10 transmissions and 2 non transmissions were observed; chi-square=5.33, 1 df, p=0.02).

The present invention therefore relates to a method of determining the susceptibility of a patient to a bipolar disorder comprising:
(a) obtaining a sample from a patient; and
(b) testing the sample for the presence of a polymorphism selected from (i) a 2 repeat allele in the variable number of tandem repeat (VNTR) region of the DRD4 gene and (ii) a 4 repeat allele in the VNTR region of the DRD4 gene, wherein the presence of the 2 repeat allele indicates that the patient is less susceptible to a bipolar disorder and the presence of the 4 repeat allele indicates that the patient is more susceptible to a bipolar disorder.

Preferably the polymorphism is transmitted from the maternal side. Therefore the present invention further relates to a method of determining the susceptibility of a patient to a bipolar disorder as defined above, further comprising:
(c) obtaining a sample from the patient's mother;
(d) testing the mother's sample for the presence of a polymorphism selected from (i) a 2 repeat allele in the variable number of tandem repeat (VNTR) region of the DRD4 gene and (ii) a 4 repeat allele in the VNTR region of the DRD4 gene, wherein the presence of a 2 repeat allele from the mother in the sample from the patient indicates that the patient is less susceptible to a bipolar disorder and the presence of a 4 repeat allele from the mother in the sample from the patient indicates that the patient is more susceptible to a bipolar disorder.

The term "repeat unit in the VNTR region of the DRD4 gene" means a 48 bp unit found in the variable number of tandem repeat (VNTR) region in the third exon of the dopamine D4 receptor (DRD4). In the 2-allele polymorphism, 2 of the 48 bp units are present and in the 4-allele polymorphism, 4 of the 48 bp units are present.

The term "bipolar disorder" refers to any type of bipolar disorder, including, but limited to, Bipolar I, Bipolar II, and Schizoaffective Bipolar-type Disorder.

The sample obtained from the patient can be any biological sample containing nucleic acids including, but not limited to, blood, urine, skin, hair, sperm, buccal mucosa as well as tissue samples and fractions of any of the foregoing.

The sample may be tested for the presence of a polymorphism in the DRD4 gene using a variety of techniques known in the art. Generally, nucleic acids are obtained from the sample and amplified using the Polymerase Chain Reaction (PCR) using primers to the appropriate region of the DRD4 gene. For example when assaying for polymorphisms in the VNTR region, primers to the VNTR are used (Lichter et al. 1993). The PCR products can be subjected to any method that would allow one to identify the presence of a polymorphism. In one embodiment, the PCR products may be subjected to an electrophoretic assay (such as gel electrophoresis or capillary electrophoresis) to determine the relative size of the PCR product. For example, the size of the PCR product can be determined by comparing its migration on an electrophoresis gel with a 50 bp ladder. Once the size has been determined in this manner, it can be compared with the predicted size of the repeat alleles to confirm its identity. In another embodiment, the PCR products may be probed with a fluorescently-labeled nucleic acid sequence specific for a region in the polymorphism. In a further embodiment, the PCR products may be sequenced using techniques known in the art including commercially available sequencing kits to determine if the polymorphism is present in the sample. Other sequencing technologies such as Denaturing High Pressure Liquid Chromatography or mass spectroscopy may also be employed. In yet another embodiment, detection of polymorphism can be performed by using restriction enzymes or Single Stranded Conformation Polymorphism (SSCP) techniques. In addition, methods for high throughput detection of nucleotide polymorphisms may be used such as DNA chip technology. Combinations of any of the above methods may be used.

The above definitions and descriptions apply to all embodiments of the present invention.

The method of the invention may also be used to detect a polymorphism in the DRD4 gene associated with a bipolar disorder. Accordingly, in a further embodiment, the present invention relates to a method of detecting the presence of a polymorphism in the DRD4 gene associated with a bipolar disorder in a patient comprising:

(a) obtaining a sample from a patient; and
(b) testing the sample for the presence of a polymorphism selected from (i) a 2 repeat allele in the variable number of tandem repeat (VNTR) region of the DRD4 gene and (ii) a 4 repeat allele in the VNTR region of the DRD4 gene, wherein the presence of the 2 repeat allele or the presence of the 4 repeat allele indicates the presence of a polymorphism in the DRD4 gene associated with bipolar disorder in the patient.

Preferably the polymorphism is transmitted from the maternal side. Therefore the present invention also relates to a method of detecting the presence of a polymorphism in the DRD4 gene associated with a bipolar disorder in a patient as defined above, further comprising:

(c) obtaining a sample from the patient's mother;
(d) testing the mother's sample for the presence of a polymorphism selected from (i) a 2 repeat allele in the variable number of tandem repeat (VNTR) region of the DRD4 gene and (ii) a 4 repeat allele in the VNTR region of the DRD4 gene, wherein the presence of a 2 repeat allele from the mother in the sample from the patient or the presence of a 4 repeat allele from the mother in the sample from the patient indicates the presence of a polymorphism in the DRD4 gene associated with a bipolar disorder in the patient.

The invention also includes kits for use in the above methods for detecting the presence of the polymorphism in the VNTR region of the DRD4 gene. Accordingly, the present invention provides a kit for determining the susceptibility of a patient to a bipolar disorder, or for determining the presence of a polymorphism in the DRD4 gene associated with a bipolar disorder, comprising reagents necessary for determining the presence of a polymorphism selected from (i) a 2 repeat allele in the VNTR region of the DRD4 gene and (ii) a 4 repeat allele in the VNTR region of the DRD4 gene and directions for its use.

The reagents useful in the kit can be determined by one of skill in the art and can include primers to the appropriate regions of the DRD4 gene in order to amplify nucleic acids from a test sample using PCR. The kit may further include nucleic acid probes useful in determining the presence of the VNTR variant. The kit may also include electrophoretic markers such as a 50 bp ladder. Other components of the kit can include nucleotides, enzymes and buffers useful in a method of the invention. As an example, a kit of the invention may include primers for amplifying the region surrounding the VNTR variant, DNA polymerase, each of dATP, dTTP, dCTP and dGTP, 7-deaza-dGTP, 10 mM Tris-HCl, 50 mM KCl, 1.5 mM $MgCl_2$ and 5% DMSO. The kit will also include detailed instructions for carrying out the method for detecting the presence of the VNTR variant of the DRD4 gene.

The following non-limiting examples are illustrative of the present invention:

EXAMPLES

Example 1

Methods (i) Subjects.

The sample was comprised of 154 individuals with a DSM-IV diagnosis of bipolar disorder (104 Bipolar I; 40 Bipolar II; 8 Schizoaffective bipolar type disorder; 2 bipolar disorder Not Otherwise Specified) and their biological relatives that comprise 145 nuclear because nine of the families have two affected probands. The probands were 103 (66.9%) female and 51 male (33.1%) in the 97% of the cases of Caucasian ethnicity with a mean age of 36.25 (SD=±9.48 range from 13 to 62) and with a mean age of onset of the disorder of 18.54 (SD=±7.08; ranging from 5 to 40). The patients were recruited from different Psychiatric Centre in the greater Toronto area. The study was approved by the University of Toronto and The Centre for Addiction and Mental Health human subject ethics committee. After complete description of the study to the subjects, written informed consent was obtained from each patient and their respective parents that agreed to participate to the study. The diagnoses were obtained after an interview with the Schedule for Affective Disorders and Schizophrenia-Lifetime Version Two, from trained staff at our Section.

(ii) Laboratory Methods.

Blood samples were drawn from patients and relatives and DNA samples were extracted from whole blood following standard procedures. The 48 base pair VNTR region in the third exon of DRD4 was amplified using PCR techniques with primers and conditions previously published (Lichter et al 1993) The PCR products containing DRD4 48 bp repeats were visualized using a gel electrophoresis performed in 3.5% agarose prepared with ethidium bromide and 1×TBE (Tris, boric acid, EDTA). An ABI Prism 310 (Perkin Elmer) was used for the fragment analysis of the TH tetranucleotide VNTR using a PCR product obtained with 5' fluorescently labeled primer with sequence previously published (Edwards et al 1992). The TH genotypes were assigned using GENOTYPER® 2.5 software that compared allele size with the size standard TAMRA (Perkin Elmer's Applied Biosystems, Warrington, England). The subjects were genotyped blind to their affection status and family structure.

(iii) Statistical Methods

The PEDMANEGER® program software (v0.9) was used to check genotypes according to the family structure in order to exclude the presence of parent-proband inconsistency and to calculate the allele frequencies. The nuclear families were tested for the presence of deviation from equal transmission of DRD4 and TH alleles using the Transmission Disequilibrium Test for mutiallelic polymorphisms as implemented by Sham and Curtis (1995) in the ETDT package (E-TDT, v1.8; Sham and Curtis, 1995). This approach tests the null hypothesis of no association by the classical McNemar test statistic for transmitted and non-transmitted parental alleles from heterozygous parents. The TDT statistic uses only parental genotypes that are heterozygous; parental genotypes that are homozygous are excluded from the analysis. Evidence for biased transmission of the alleles was searched using the allele-wise and genotype-wise analysis that allows to investigate, for multiallelic polymorphisms, whether a departure from the null hypothesis exist. Because this analysis in the data set indicated a statistically significant departure from the null hypothesis, the transmission for each allele individually was examined in order to understand which allele was contributing to the biased transmission observed considering all the alleles together (allele-wise and genotype-wise analyses). The alleles with a frequency less than 4% were not considered in the analysis of the transmission for individual alleles because of the low power that can be obtained by their analysis. Furthermore, in order to understand whether the transmission of the biased alleles observed were derived differently from the maternal or the paternal meiosis, parent-sex-specific analysis of the transmission of the alleles was performed. Because multiple tests were performed to analyze the transmission of each allele individually and to calculate maternal and paternal transmission separately correction for multiple testing have to be considered. In the search of genes for complex diseases however, it is not known to what extend multiple testing increases the false positive rate.

There is a lack of methods that appropriately correct for not using independent multiple testing. The Bonferroni correction approach is the most stringent criteria for correction and it was decided to correct using this method in order to somehow correct the presence of false positives derived from multiple testing. The twelve tests conducted (for the alleles with the frequency above 4% five tests were performed to analyze individually the transmission of the TH alleles and three tests for the DRD4 VNTR alleles plus four tests conducted to explore the maternal and paternal meiosis independently for each of the two genes) were corrected.

In addition to the TDT analysis, the Haplotype Relative Risk (HRR) statistic analysis (Falk C. and Rubinstein 1987) was applied. This is a standard chi-squared statistic that, differently from TDT, uses all parental genotypes and classifies each parent according to which allele is transmitted and which is not (for the homozygous parents the same allele is scored as transmitted and non-transmitted). The HRR statistic compares how many times a given parental allele (high- or low-risk) is transmitted versus non-transmitted. Because the variance estimate for HRR uses more information than does the variance estimate for the TDT/McNemar statistic, it can lead to a more powerful statistical test for association; however, under certain conditions, HRR could be less powerful than the TDT/McNemar test (Schaid and Sommer 1994). Furthermore, because HRR uses all the transmitted and non-transmitted alleles the HRR contingency two by two tables (obtained computing the transmission and non transmission of the alleles) allows to calculate the odds ratios for the "risk" and "non-risk" alleles. Because the polymorphism studied were multiallelic, the two by two HRR tables were obtained considering in one column the transmissions and non-transmissions of the "risk" allele (or the "non risk" allele) while the transmissions and non-transmission for all the others alleles were grouped in the other column. The alleles that the TDT analyses showed to be biased were considered in the HRR tables. The odds ratio (that is approximately equal to the relative risk) provide an estimation for the risk associate with the transmission of a given allele.

Results

The results of the transmission of the individual alleles from the heterozygous parent to the affected off-springs of the HUMTH01 and DRD4 VNTR alleles are indicated in the Table 1.The analysis of the transmission for HUMTH01 did not reveal preferential transmission for any of the alleles nor maternal or paternal preferential transmission. TDT analysis for DRD4 VNTR revealed biased transmission of the 4 and 2 repeats alleles. Genotypes in the parents containing the 2 repeat allele occurred 40 times and the 2 repeat alleles were transmitted only 12 times to the affected offspring (chi-square for genotype-wise=14.84; df=8; p=0.062; chi-square for allele-wise=10.32; df=5; p=0.066). The results from the analysis of the transmissions for individual alleles of DRD4 indicates that the 2 repeat allele exhibited an excess of non-transmission to the affected offspring (12 times transmitted vs. 28 times non-transmitted, chi-square=6.40; df=1; nominal p value=0.0114). On the other hand the analysis of the 4 repeats alleles revealed an excess of transmission for this alleles (77 times transmitted vs. 52 non-transmitted chi-square=4.845 df=1; nominal p value=0.0278). The separate analysis of the individual alleles from maternal and paternal meioses revealed that the biased transmission for the 2 and 4 repeats alleles were derived mostly from maternal meiosis. In fact, the 2 repeat allele was maternally transmitted only twice while this allele was not transmitted 16 times (chi-square=10.889; df=1; nominal p=0.0010) and the 4 repeat was transmitted 40 times and non transmitted 20 times (chi-square=6.667; df=1; nominal p=0.009). Whereas the same alleles did not show biased transmission when the paternal meiosis were considered. The statistically significant level at p=0.01 was maintained after correction for multiple testing with Bonferroni test for the biased transmission of the 2 repeat (p=0.012). In the Table 2 the results from the HRR analysis are shown as well as the odds ratios associated with the transmission and non-transmission of the DRD4 4 and 2 repeats alleles. The odds ratios indicate that the 4 repeats alleles are increasing the risk to suffer from bipolar disorder (Odds Ratio=1.7; C. I. (95%)=1.18–2.46; P=0.002), while the 2 repeat alleles is associated with a protective effect (Odds Ratio=0.44; C. I. (95%)=0.22–0.86; P=0.010). The analyses of the maternal and paternal transmissions clearly indicates that the risk associated with the 4 repeat alleles is derived almost exclusively from the maternal meiosis (Odds Ratio=2.34; C. I. (95%)=1.29–4.26; P=0.0038) when compared to the risk associated from the transmission from the paternal side (Odds Ratio=1.25; C. I. (95%)=0.69–2.27; P=0.2). In a similar way, the protective effect associated with the non-transmission of the 2 repeat alleles is exclusively of maternal origin (Odds Ratio=0.15; C. I. (95%)=0.04–0.52, P=0.000619) when compared to the effect of paternal origin (Odds Ratio=0.78, C. I. (95%) =0.29–2.08, P=0.4).

Discussion

The results of the present study showed an increased number of non-transmitted DRD4 2 repeat alleles and an increased number of transmissions for the 4 repeat alleles when compared to what we should expect by chance. This effect was derived almost exclusively from the maternal meiosis. The excess of non-transmission of the 2 alleles to bipolar patients is suggesting that the 2 repeat allele may confer a protective role while the 4 repeats alleles may increase the risk in developing bipolar disorder only when transmitted from the maternal side. HUMTH01 alleles conversely did not show significant departure from the 50% expected chance to be transmitted from the parents to the affected offspring.

Different linkage analysis (De bruyn 1994), unrelated case-control and (Lim et al 1995; Perez de Castro et al 1994; Oruc et al 1997; Weiss et al 1996; Serretti et al 1999,) and a family-based association studies (Bocchetta et al 1999) have investigated the role of DRD4 exon III VNTR in bipolar disorder and none of them have shown an effect similar to what was observed in the present study. This discrepancy of the results between previous studies and present finding may be due to the presence of genetic heterogeneity and or to the different genetic structure of the population studied. The only family-based association study of DRD4 and bipolar disorder present in the literature was conducted in the genetically peculiar population from Sardinia (Bocchetta et al 1999).

Similarly, to the results reported in the present study for the transmission of HUMTH01 alleles majority of studies (see Furlong et al 1999) have failed to detect association with this polymorphism and bipolar disorder excluding a major role of HUMTH01 alleles in bipolar disorder.

In regard of the results from the present study, that shows a maternal specific biased transmission for the DRD4 VNTR alleles, it is important to consider that several lines of evidence from clinical (Grigoroiu-Serbanescu et al 1995; McMahon et al 1995; Gershon et al 1996), and molecular genetic studies (Stine et al 1995; Gershon et al 1996) suggesting that a sex-specific parent of origin effect (POE) may be involved in the transmission of bipolar disorder. Clinical studies that investigated the POE in bipolar disorder were not uniformly consistent. Grigoroiu-Serbanescu and colleagues (1995) showed that bipolar patients with an affected father had lower age of onset when compared with the onset of individuals who had a mother affected. On the other hand, other studies have suggested a prevalent matrilinear transmission (McMahon et al 1995; Gershon et al 1996). The presence of a sex-specific POE in the transmission of bipolar disorder may be determined by the presence of a risk alleles in the mitochondrial DNA or in the X chromosome or to the presence of genomic imprinting for the disease allele. The recent sequencing of the mitochondrial DNA in individuals that inherited the disorder from the mother excluded a mitochondrial DNA contribution, at least in the analyzed subjects (McMahon et al 2000). The presence of X-linked risk alleles with a major effect in bipolar disorder can be excluded from the results of linkage studies (reviews in Paterson 1999). However, since results from markers on the Xq26–28 are still inconsistent and because few association studies of candidate genes locate on the X chromosome have been conducted the presence of a gene with a small contribution for bipolar disorder on Chromosome X cannot completely ruled out yet.

Genomic imprinting defines an epigenetic phenomenon where genes are regulated depending on their parental origin. The presence of imprinting for a diseases risk allele may be the cause of a POE in the transmission of the risk allele (Hall 1990). This phenomenon has been detected in the regulation and transmission of genes for neuropsychiatric diseases such as Prader-Willi and Angelman syndromes (Cassidy and Shwarz 1998). Involvement of genomic imprinting in psychiatric diseases, that includes bipolar disorder, has been recently matter of discussion in the literature (Petronis 2000). Chromosome 18 markers have shown evidence for linkage in bipolar families, and some of these markers have shown the presence of a POE in two studies (Stine et al 1995; McMahon et al 1997). These studies have shown a paternal specific effect for two markers (D18S41 and D18S541) on 18q21 (Stine et al 19951384; McMahon et al 1997) and a maternal specific effect for another marker (D18S464) on 18p (Stine et al 1995). However, Van Broeckhoven and Verheyen (1998, 1999) were unable to replicate these findings rendering a conclusion on the POE of chromosome 18 and bipolar disorder still elusive.

Interestingly, DRD4 and TH are located on the telomeric region of the chromosome 11 close to a cluster of imprinted genes. DRD4 is approximately 200 kb telomeric to H19 the most close imprinted gene (Zhang et al 1992) while TH is 9 kb centromeric to an imprinted region flanking the insulin-like growth factor 2 (IGF2) gene and the insulin gene (INS) (Giannoukakis et al 1993). Because imprinted genes tend to cluster DRD4 expression was tested for monoallelic expression in the temporal cortex of two patients (Cichon et al 1996). The study showed expression of both maternal and paternal alleles of DRD4. The expression of both DRD4 alleles in this study however did not completely exclude the presence of imprinting for DRD4 because imprinting can be developmental stage- and tissue specific phenomenon as well as in some cases polymorphic (Hall 1997). Because these complexities genomic imprinting is a multifaceted phenomenon described only recently in mammals with function and mechanism not fully understood (Tilgham 1999).

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

|   | TH tetranucleotide VNTR alleles | | | | | | DRD4 48 bp repeat VNTR alleles | | | | Maternal Meiosis | | Paternal Meiosis | |
|---|---|---|---|---|---|---|---|---|---|---|---|---|---|---|
|   | A2 | A3 | A4 | A5 | A6 | RA | [a]A2 | [b]A4 | A7 | RA | [c]A2 | [d]A4 | A2 | A4 |
| T | 38 | 27 | 21 | 21 | 39 | 1 | 12 | 77 | 40 | 11 | 2 | 40 | 8 | 26 |
| N-T | 32 | 30 | 17 | 28 | 42 | 0 | 28 | 52 | 49 | 11 | 16 | 20 | 10 | 21 |

Transmitted (T) and non-transmitted (N-T) alleles. The symbols for TH: A2, A3, A4, A5, A6 represent Alleles 2, 3, 4, 5 and 6 and RA represent Rare Allele 1. For the DRD4 the symbols A2, A4, and A7 represent 48 bp repeat polymorphism of 2, 4, and 7 repeats respectively. The Rare Alleles (RA) group consists of 3, 5 and 6 repeats for DRD4 and for TH.
[a]$\chi2 = 6.4$, df = 1; p = 0.0114
[b]$\chi2 = 4.845$, df = 1; p = 0.0278
[c]$\chi2 = 10.889$; df = 1; p = 0.0010
[d]$\chi2 = 6.667$; df = 1; p = 0.0099
p values are not corrected for multiple testing

TABLE 2

| Alleles | Odds Ratio | 95% Confidence interval | P value |
|---|---|---|---|
| 4R vs. Non 4R | 1.7 | 1.18–2.46 | 0.002 |
| 2R vs. Non 2R | 0.44 | 0.22–0.86 | 0.010 |
| Maternal Meiosis | | | |
| 4R vs. Non 4R | 2.34 | 1.29–4.26 | 0.0038 |
| 2R vs. Non 2R | 0.15 | 0.04–0.52 | 0.000619 |
| Paternal Meiosis | | | |
| 4R vs. Non 4R | 1.25 | 0.69–2.27 | 0.2 |
| 2R vs. Non 2R | 0.78 | 0.29–2.08 | 0.4 |

Haplotype Relative Risk of the DRD4 48 bp repeats VNTR alleles

| | 4-R | Non -4R |
|---|---|---|
| Transmitted | 190 | 71 |
| Non-Transmitted | 165 | 105 |

Odds Ratio = 1.7
C.I. (95%) = 1.18–2.46
P = 0.002

| | 2-R | Non -2R |
|---|---|---|
| Transmitted | 13 | 248 |
| Non-Transmitted | 29 | 241 |

Odds Ratio = 0.44
C.I. (95%) = 0.22–0.86
P = 0.010

Haplotype Relative Risk Maternal Meiosis

| | 4-R | Non -4R |
|---|---|---|
| Transmitted | 65 | 29 |
| Non-Transmitted | 45 | 47 |

Odds Ratio = 2.34
C.I. (95%) = 1.29–4.26
P = 0.0038

| | 2-R | Non -2R |
|---|---|---|
| Transmitted | 3 | 91 |
| Non-Transmitted | 17 | 75 |

Odds Ratio = 0.15
C.I. (95%) = 0.04–0.52
P = 0.000619
This O.R. indicate to what extend the 2 repeat allele is protective
If we consider the risk given by the transmission of the Non-2-repeat alleles we have: O.R. = 6.88; C.I. (95%) = 1.94–24.36;
P = 0.000619

Haplotype Relative Risk Paternal Meiosis

| | 4-R | Non -4R |
|---|---|---|
| Transmitted | 56 | 35 |
| Non-Transmitted | 51 | 40 |

Odds Ratio = 1.25
C.I. (95%) = 0.69–2.27
P = 0.2

| | 2-R | Non -2R |
|---|---|---|
| Transmitted | 8 | 83 |
| Non-Transmitted | 10 | 81 |

Odds Ratio = 0.78
C.I. (95%) = 0.29–2.08
P = 0.4

Transmission of the DRD4 48 bp 2 and 4 4 repeats alleles and estimation of relative risks associated with the transmission of this alleles. The analyses include the estimation of the risk derived from the transmission of the alleles from the maternal and from the paternal meiosis (for more details see text in the statistical analysis paragraph) are derived by the Haplotype Relative Risks analysis. HRR allows to calculate the Odds Ratio because the non transmitted alleles are considered as controls. Below this table the two by two contingency tables from the HRR analysis are illustrated. All the p value indicated here are two-tail and represent the most conservative approach.

Full Citations for References Referred to in the Specification

Asghari, V., S. Sanyal, et al. (1995). "Modulation of intracellular cyclic AMP levels by different human dopamine D4 receptor variants." *J Neurochem* 65(3): 1157–65.

Berrettini, W. H. (1999). "On the future of genetic research in bipolar and schizophrenic syndromes." *Neuropsychopharmacology* 21(1): 1–2.

Bocchetta, A., M. P. Piccardi, et al. (1999). "Family-based association study between bipolar disorder and DRD2, DRD4, DAT, and SERT in Sardinia." *Am J Med Genet* 88(5): 522–6.

Byerley, W., R. Plaetke, et al. (1992). "Tyrosine hydroxylase gene not linked to manic-depression in seven of eight pedigrees." *Hum Hered* 42(4): 259–63.

Cassidy, S. B. and S. Schwartz (1998). "Prader-Willi and Angelman syndromes. Disorders of genomic imprinting." *Medicine (Baltimore)* 77(2): 140–51.

Chang, F. M., J. R. Kidd, et al. (1996). "The world-wide distribution of allele frequencies at the human dopamine D4 receptor locus." *Hum Genet* 98(1): 91–101.

Cichon, S., M. M. Nothen, et al. (1996). "Lack of imprinting of the human dopamine D4 receptor (DRD4) gene." *Am J Med Genet* 67(2): 229–31.

De bruyn, A., K. Mendelbaum, et al. (1994). "Nonlinkage of bipolar illness to tyrosine hydroxylase, tyrosinase, and D2 and D4 dopamine receptor genes on chromosome 11." *Am J Psychiatry* 151(1): 102-6.

Detera-Wadleigh, S. D., W. H. Berrettini, et al. (1987). "Close linkage of c-Harvey-ras-1 and the insulin gene to affective disorder is ruled out in three North American pedigrees." *Nature* 325(6107): 806–8.

Ding, Y. C., H. C. Chi, et al. (2002). "Evidence of positive selection acting at the human dopamine receptor D4 gene locus." *Proc Natl Acad Sci US A* 99(1): 309–14.

Edwards, A., H. A. Hammond, et al. (1992). "Genetic variation at five trimeric and tetrameric tandem repeat loci in four human population groups." *Genomics* 12(2): 241–53.

Egeland, J. A., D. S. Gerhard, et al. (1987). "Bipolar affective disorders linked to DNA markers on chromosome 11." *Nature* 325(6107): 783–7.

Falk, C. T. and P. Rubinstein (1987). "Haplotype relative risks: an easy reliable way to construct a proper control sample for risk calculations." *Ann Hum Genet* 51 (Pt 3): 227–33.

Furlong, R. A., J. S. Rubinsztein, et al. (1999). "Analysis and metaanalysis of two polymorphisms within the tyrosine hydroxylase gene in bipolar and unipolar affective disorders." *Am J Med Genet* 88(1): 88–94.

Gershon, E. S., J. A. Badner, et al. (1996). "Maternal inheritance and chromosome 18 allele sharing in unilineal bipolar illness pedigrees."*Am J Med Genet* 67(2): 202–7.

Gershon, E. S., M. Martinez, et al. (1990). "Genetic mapping of common diseases: the challenges of manic-depressive illness and schizophrenia [see comments]." Trends Genet (9): 282–7.

Giannoukakis, N., C. Deal, et al. (1993). "Parental genomic imprinting of the human IGF2 gene." Nat Genet 4(1): 98–101.

Greenberg, D. A. (1993). "Linkage analysis of "necessary" disease loci versus "susceptibility" loci." Am J Hum Genet 52(1): 135–43.

Grigoroiu-Serbanescu, M., M. Nothen, et al. (1995). "Clinical evidence for genomic imprinting in bipolar I disorder." Acta Psychiatr Scand 92(5): 365–70.

Hall, J. G. (1990). "Genomic imprinting: review and relevance to human diseases." Am J Hum Genet 46(5): 857–73.

Jovanovic, V., H. C. Guan, et al. (1999). "Comparative pharmacological and functional analysis of the human dopamine D4.2 and D4.10 receptor variants." Pharmacogenetics 9(5): 561–8.

Kelsoe, J. R., E. I. Ginns, et al. (1989). "Re-evaluation of the linkage relationship between chromosome 11p loci and the gene for bipolar affective disorder in the Old Order Amish [see comments]." Nature 342(6247): 238–43.

Kidd, K. K. (1993). "Associations of disease with genetic markers: deja vu all over again [editorial]." Am J Med Genet 48(2): 71–3.

Li, T., X. Liu, et al. (1999). "Association analysis between dopamine receptor genes and bipolar affective disorder." Psychiatry Res 86(3): 193–201.

Lichter, J. B., C. L. Barr, et al. (1993). "A hypervariable segment in the human dopamine receptor D4 (DRD4) gene." Hum Mol Genet 2(6): 767–73.

Lim, L. C., M. M. Nothen, et al. (1994). "No evidence of association between dopamine D4 receptor variants and bipolar affective disorder." Am J Med Genet 54(3): 259–63.

Malafosse, A., M. Leboyer, et al. (1997). "Manic depressive illness and tyrosine hydroxylase gene: linkage heterogeneity and association."Neurobiol Dis 4(5): 337–49.

McMahon, F. J., Y. S. Chen, et al. (2000). "Mitochondrial DNA sequence diversity in bipolar affective disorder."Am J Psychiatry 157(7): 1058–64.

McMahon, F. J., O. C. Stine, et al. (1995). "Patterns of maternal transmission in bipolar affective disorder."Am J Hum Genet 56(6): 1277–86.

Meloni, R., V. Albanese, et al. (1998). "A tetranucleotide polymorphic microsatellite, located in the first intron of the tyrosine hydroxylase gene, acts as a transcription regulatory element in vitro." Hum Mol Genet 7(3): 423–8.

Nothen, M., J. Korner, et al. (1990). "Tyrosine hydroxylase polymorphisms and manic-depressive illness [letter; comment]." Lancet 336(8714): 575.

Oruc, L., G. R. Verheyen, et al. (1997). "Analysis of the tyrosine hydroxylase and dopamine D4 receptor genes in a Croatian sample of bipolar I and unipolar patients." Am J Med Genet 74(2): 176–8.

Ott, J. (1999). Analysis of human genetic linkage. Baltimore and London, The John Hopkins University Press.

Paterson, A. D. (1999). "Sixth World Congress of Psychiatric Genetics X Chromosome Workshop." Am J Med Genet 88(3): 279–86.

Perez de Castro, I., P. Torres, et al. (1994). "No association between dopamine D4 receptor polymorphism and manic depressive illness." J Med Genet 31(11): 897–8.

Petronis, A. (2000). "The genes for major psychosis: aberrant sequence or regulation?" Neuropsychopharmacology 23(1): 1–12.

Polymeropoulos, M. H., H. Xiao, et al. (1991). "Tetranucleotide repeat polymorphism at the human tyrosine hydroxylase gene (TH)." Nucleic Acids Res 19(13): 3753.

Puers, C., H. A. Hammond, et al. (1993). "Identification of repeat sequence heterogeneity at the polymorphic short tandem repeat locus HUMTH01[AATG]n and reassignment of alleles in population analysis by using a locus-specific allelic ladder." Am J Hum Genet 53(4): 953–8.

Risch, N. and D. Botstein (1996). "A manic depressive history [news]." Nat Genet 12(4): 351–3.

Risch, N. J. (2000). "Searching for genetic determinants in the new millennium." Nature 405(6788): 847–56.

Schaid, D. J. and S. S. Sommer (1994). "Comparison of statistics for candidate-gene association studies using cases and parents." Am J Hum Genet 55(2): 402–9.

Serretti, A., R. Lilli, et al. (1999). "Dopamine receptor D4 gene is not associated with major psychoses." Am J Med Genet 88(5): 486–91.

Sham, P. C. and D. Curtis (1995). "An extended transmission/disequilibrium test (TDT) for multi-allele marker loci." Ann Hum Genet 59(Pt 3): 323–36.

Sidenberg, D. G., N. King, et al. (1994). "Analysis of new D4 dopamine receptor (DRD4) coding region variants and TH microsatellite in the Old Order Amish family (OOA110)." Psychiatr Genet 4(2): 95–9.

Smyth, C., G. Kalsi, et al. (1996). "Further tests for linkage of bipolar affective disorder to the tyrosine hydroxylase gene locus on chromosome 11p15 in a new series of multiplex British affective disorder pedigrees [published erratum appears in Am J Psychiatry January 1997 ;154 (1):139]." Am J Psychiatry 153(2): 271–4.

Smyth, C., G. Kalsi, et al. (1997). "Two-locus admixture linkage analysis of bipolar and unipolar affective disorder supports the presence of susceptibility loci on chromosomes 11p15 and 21q22." Genomics 39(3): 271–8.

Stine, O. C., J. Xu, et al. (1995). "Evidence for linkage of bipolar disorder to chromosome 18 with a parent-of-origin effect." Am J Hum Genet 57(6): 1384–94.

Tilghman, S. M. (1999). "The sins of the fathers and mothers: genomic imprinting in mammalian development." Cell 96(2): 185–93.

Van Broeckhoven, C. and G. Verheyen (1998). "Chromosome 18 workshop." Psychiatr Genet 8(2): 97–108.

Van Broeckhoven, C. and G. Verheyen (1999). "Report of the chromosome 18 workshop." Am J Med Genet 88(3): 263–70.

Van Tol, H. H., C. M. Wu, et al. (1992). "Multiple dopamine D4 receptor variants in the human population [see comments]." Nature 358(6382): 149–52.

Weiss, J., H. J. Magert, et al. (1996). "Association between different psychotic disorders and the DRD4 polymorphism, but no differences in the main ligand binding region of the DRD4 receptor protein compared to controls." Eur J Med Res 1(9): 439–45.

Willner, P. (1995). Dopaminergic Mechanisms in Depression and Mania, New York: Raven Press, c1995.

Zhang, Y. and B. Tycko (1992). "Monoallelic expression of the human H19 gene." Nat Genet 1(1): 40–4.

We claim:

1. A method of determining the susceptibility of a patient to a bipolar disorder comprising:
   (a) obtaining a sample from a patient; and
   (b) testing the sample for the presence of a polymorphism selected from (i) a 2 repeat allele in the variable number of tandem repeat (VNTR) region of the DRD4 gene and (ii) a 4 repeat allele in the VNTR region of the DRD4 gene, wherein the VNTR region is a 48bp unit found in the third exon of the DRD4 gene and wherein the presence of the 2 repeat allele indicates that the patient is less susceptible to a bipolar disorder and the presence of the 4 repeat allele indicates that the patient is more susceptible to a bipolar disorder.

2. The method according to claim 1, further comprising the steps of:
(c) obtaining a sample from the patient's mother; and
(d) testing the mothers sample for the presence of a polymorphism selected from (i) a 2 repeat allele in the variable number of tandem repeat (VNTR) region of the DRD4 gene and (ii) a 4 repeat allele in the VNTR region of the DRD4 gene, wherein the presence of a 2 repeat allele from the mother in the sample from the patient indicates that the patient is less susceptible to a bipolar disorder and the presence of a 4 repeat allele from the mother in the sample from the patient indicates that the patient is more susceptible to a bipolar disorder.

3. The method according to claim 2 wherein step (d) comprises (i) extracting nucleic acids from the sample; (ii) amplifying the extracted nucleic acids using polymerase chain reaction (PCR); (iii) performing electrophoresis of the PCR products; and (iv) determining the presence of the polymorphism.

4. The method according to claim 1, wherein the sample is blood.

5. The method according to claim 1, wherein step (b) comprises (i) extracting nucleic acids from the sample; (ii) amplifying the extracted nucleic acids using polymerase chain reaction (PCR); (iii) performing electrophoresis of the PCR products; and (iv) determining the presence of the polymorphism.

6. A method of detecting the presence of a polymorphism in the DRD4 gene associated with a bipolar disorder in a patient comprising:

(a) obtaining a sample from the patient; and
(b) testing the sample for the presence of a polymorphism selected from (i) a 2 repeat allele in the variable number of tandem repeat (VNTR) region of the DRD4 gene and (ii) a 4 repeat allele in the VNTR region of the DRD4 gene, wherein the VNTR region is a 48bp unit found in the third exon of the DRD4 gene and wherein the presence of the 2 repeat allele or the presence of the 4 repeat allele indicates the presence of a polymorphism in the DRD4 gene associated with bipolar disorder in the patient.

7. The method according to claim 6, further comprising the steps of
(c) obtaining a sample from the patient's mother; and
(d) testing the mothers sample for the presence of a polymorphism selected from (i) a 2 repeat allele in the variable number of tandem repeat (VNTR) region of the DRD4 gene and (ii) a 4 repeat allele in the VNTR region of the DRD4 gene, wherein the presence of a 2 repeat allele from the mother in the sample from the patient or the presence of a 4 repeat allele from the mother in the sample from the patient indicates the presence of a polymorphism in the DRD4 gene associated with a bipolar disorder in the patient.

8. The method according to claim 7 wherein step (d) comprises (i) extracting nucleic acids from the sample; (ii) amplifying the extracted nucleic acids using polymerase chain reaction (POR); (iii) performing electrophoresis of the PCR products; and (iv) determining the presence of the polymorphism.

9. The method according to claim 6, wherein the sample is blood.

10. The method according to claim 6 wherein step (b) comprises (i) extracting nucleic acids from the sample; (ii) amplifying the extracted nucleic acids using polymerase chain reaction (PCR); (iii) performing electrophoresis of the PCR products; and (iv) determining the presence of the polymorphism.

* * * * *